(12) United States Patent
Sun et al.

(10) Patent No.: US 10,363,343 B2
(45) Date of Patent: Jul. 30, 2019

(54) TISSUE-BASED DRAIN MANIFOLDS

(71) Applicant: LifeCell Corporation, Branchburg, NJ (US)

(72) Inventors: Wenquan Sun, Warrington, PA (US); Nathaniel Bachrach, Clifton, NJ (US); Mark Hayzlett, Flemington, NJ (US)

(73) Assignee: LifeCell Corporation, Madison, NJ (US)

( * ) Notice: Subject to any disclaimer, the term of this patent is extended or adjusted under 35 U.S.C. 154(b) by 733 days.

(21) Appl. No.: 14/410,199

(22) PCT Filed: Jul. 1, 2013

(86) PCT No.: PCT/US2013/048918
§ 371 (c)(1),
(2) Date: Dec. 22, 2014

(87) PCT Pub. No.: WO2014/008184
PCT Pub. Date: Jan. 9, 2014

(65) Prior Publication Data
US 2015/0320911 A1    Nov. 12, 2015

Related U.S. Application Data

(60) Provisional application No. 61/668,189, filed on Jul. 5, 2012.

(51) Int. Cl.
*A61M 27/00* (2006.01)
*A61L 31/00* (2006.01)
(Continued)

(52) U.S. Cl.
CPC ............. *A61L 31/005* (2013.01); *A61L 31/06* (2013.01); *A61L 31/16* (2013.01); *A61M 27/00* (2013.01);
(Continued)

(58) Field of Classification Search
CPC .......... A61L 31/00; A61L 31/16; A61L 31/06; A61M 27/00; A61M 22/00; A61M 22/04; A61M 1/00
See application file for complete search history.

(56) References Cited

U.S. PATENT DOCUMENTS 4,233,969 A    11/1980 Lock et al.
4,373,519 A    2/1983 Errede et al.
(Continued)

FOREIGN PATENT DOCUMENTS

EP    1415671 A1    5/2004
GB    1446766 A    8/1976
(Continued)

OTHER PUBLICATIONS

Argenta et al., "Vacuum-Assisted Closure: A New Method for Wound Control and Treatment: Clinical Experience," Annals of Plastic Surgery. vol. 38, No. 6, pp. 563-577, 1997.
(Continued)

*Primary Examiner* — Tatyana Zalukaeva
*Assistant Examiner* — Ilya Y Treyger
(74) *Attorney, Agent, or Firm* — McCarter & English, LLP (57) ABSTRACT

Disclosed herein are tissue-based drain manifolds comprising partially or completely decellularized tissue that has been processed to form tubes, columns, sheets, or other shapes and which are useful for managing the drainage of fluid and/or the administration of negative pressure at an implant site in a patient. The manifolds can be implanted in a patient and provide a natural scaffold in which native cells from surrounding tissue can migrate and proliferate, thereby avoiding the need to remove the implanted manifolds after drainage is complete.

16 Claims, 4 Drawing Sheets

(51) Int. Cl.
*A61L 31/16* (2006.01)
*A61L 31/06* (2006.01)
*A61M 1/00* (2006.01)

(52) U.S. Cl.
CPC .......... *A61L 2430/40* (2013.01); *A61M 1/009* (2014.02); *A61M 2202/0014* (2013.01); *A61M 2205/04* (2013.01); *A61M 2207/00* (2013.01)

(56) References Cited

U.S. PATENT DOCUMENTS

| | | | |
|---|---|---|---|
| 4,569,348 A | 2/1986 | Hasslinger | |
| 5,149,331 A | 9/1992 | Ferdman et al. | |
| 5,263,971 A | 11/1993 | Hirshowitz et al. | |
| 5,298,015 A | 3/1994 | Komatsuzaki et al. | |
| 5,336,616 A | 8/1994 | Livesey et al. | |
| 5,364,756 A | 11/1994 | Livesey et al. | |
| 5,437,651 A | 8/1995 | Todd et al. | |
| 5,549,584 A | 8/1996 | Gross | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,184,037 B1* | 2/2001 | Rolland | A61K 47/4823 435/455 |
| 6,345,623 B1 | 2/2002 | Heaton et al. | |
| 6,553,998 B2 | 4/2003 | Heaton et al. | |
| 6,814,079 B2 | 11/2004 | Heaton et al. | |
| 6,933,326 B1 | 8/2005 | Griffey et al. | |
| 7,198,046 B1 | 4/2007 | Argenta et al. | |
| 7,498,040 B2 | 3/2009 | Masinaei et al. | |
| 7,498,041 B2 | 3/2009 | Masinaei et al. | |
| 7,968,026 B1* | 6/2011 | Teoh | A61L 27/18 264/113 |
| 8,324,449 B2 | 12/2012 | McQuillan et al. | |
| 9,259,511 B2* | 2/2016 | Sun | A61L 27/362 |
| 2002/0120185 A1 | 8/2002 | Johnson | |
| 2003/0035843 A1 | 2/2003 | Livesey et al. | |
| 2003/0036636 A1 | 2/2003 | Huang et al. | |
| 2003/0143207 A1 | 7/2003 | Livesey et al. | |
| 2004/0028738 A1 | 2/2004 | Huang et al. | |
| 2005/0028228 A1 | 2/2005 | McQuillan et al. | |
| 2005/0043819 A1 | 2/2005 | Schmidt et al. | |
| 2005/0159822 A1 | 7/2005 | Griffey et al. | |
| 2006/0073592 A1 | 4/2006 | Sun et al. | |
| 2006/0127375 A1 | 6/2006 | Livesey et al. | |
| 2006/0210960 A1 | 9/2006 | Livesey et al. | |
| 2007/0219471 A1 | 9/2007 | Johnson et al. | |
| 2007/0248575 A1 | 10/2007 | Connor et al. | |
| 2008/0027542 A1 | 1/2008 | McQuillan et al. | |
| 2009/0035289 A1 | 2/2009 | Wagner et al. | |
| 2010/0040687 A1 | 2/2010 | Pedrozo et al. | |
| 2010/0161054 A1 | 6/2010 | Park et al. | |
| 2012/0010728 A1 | 1/2012 | Sun et al. | |
| 2012/0310367 A1* | 12/2012 | Connor | A61K 35/35 623/23.72 |

FOREIGN PATENT DOCUMENTS

| | | |
|---|---|---|
| WO | WO-2002/40630 A2 | 5/2002 |
| WO | WO-2009/155600 A2 | 12/2009 |
| WO | WO-2012/166784 A1 | 12/2012 |

OTHER PUBLICATIONS

Australian Examination Report issued in AU Patent Application No. 2009281937, dated Aug. 5, 2014, 5 pgs.

Blackburn II et al., "Negative-Pressure Dressings as a Bolster for Skin Grafts," Annals of Plastic Surgery, vol. 40, No. 5, pp. 453-457, 1998.

Brandi et al., "Treatment with vacuum-assisted closure and cryo-preserved homologous de-epidermalised dermis of complex traumas to the lower limbs with loss of substance, and bones and tendons exposure," Journal of Plastic, Reconstructive and Aesthetic Surgery, vol. 61, pp. 1507-1511.

Chariker et al., "Effective management of incisional and cutaneous fistulae with closed suction wound drainage," Contemporary Surgery, vol. 34, pp. 59-64, 1989.

Chinn et al., "Closed Wound Suction Drainage," The Journal of Foot Surgery, vol. 24, pp. 76-81, 1985.

Dattilo et al., "Medical Textiles: Application of an Absorbable Barbed Bi-directional Surgical Suture," Journal of Textile and Apparel, Technology and Management, vol. 2, Issue 2, pp. 1-5, 2002.

DeFranzo et al., "Vaccum-Assisted Closure for the Treatment of Abdominal Wounds," Clinics in Plastic Surgery, vol. 33, pp. 213-224, 2006.

Examination Report issued by the European Patent Office for European Application No. 11153969.8 dated Apr. 9, 2013 (3 pages).

Flack et al., "An economic evaluation of VAC therapy compared with wound dressings in the treatment of diabetic foot ulcers," Journal of Wound Care, vol. 17, No. 2, pp. 71-78, 2008.

Griffey et al., "Particulate Dermal Matrix as an Injectable Soft Tissue Replacement Material," J. Biomed. Mater. Res. (Appl. Biomater), vol. 58, pp. 10-15, 2001.

KCI Licensing, Inc. "V.A.C.® Therapy Safety Information," pp. 1-4, 2007.

Masters et al., "Reliable, inexpensive and simple suction dressings," Letters to the Editor, British Journal of Plastic Surgery, vol. 51, No. 3, p. 267, 1998.

O'Connor et al., "Vacuum-Assisted Closure for the Treatment of Complex Chest Wounds," Ann. Thorac. Surg., vol. 79, pp. 1196-1200, 2005.

Randall et al., "Use of an Acellular Regenerative Tissue Matrix in Combination with Vacuum-assisted Closure Therapy for Treatment of a Diabetic Foot Wound," The Journal of Foot and Ankle Surgery, vol. 47, No. 5, pp. 430-433, 2008.

Wei et al., "Construction of varying porous structures in acellular bovine pericardia as a tissue-engineering extracellular matrix," Biomaterials, vol. 26, pp. 1905-1913, 2005.

Yang et al., "A cartilage ECM-derived 3-D porous acellular matrix scaffold for in vivo cartilage tissue engineering with PKH26-labeled chondrogenic bone marrow-derived mesenchymal stem cells," Biomaterials, vol. 29, pp. 2378-2387, 2008.

* cited by examiner

TISSUE-BASED DRAIN MANIFOLDS

This application is a 35 U.S.C. § 371 national stage filing of International Application No. PCT/US2013/048918, filed on Jul. 1, 2013, which claims the benefit of priority under 35 U.S.C. § 119 to U.S. Provisional Patent Application No. 61/668,189, filed on Jul. 5, 2012, the content of each of which is incorporated herein by reference in its entirety.

The present disclosure relates generally to methods of making and using tissue-based compositions as implantable drain manifolds.

Management of bodily fluids during wound treatment or after surgical intervention is an issue commonly addressed by medical professionals. The failure to adequately drain fluids can lead to seroma and/or hematoma formation. A seroma is a pocket of clear or yellow serous fluid originating from serous glands. A hematoma, in contrast, is a localized collection of blood outside a blood vessel. Both can result from trauma, such as a blow or fall, as well as from disease or surgical procedures. Seromas and hematomas are common after plastic surgery, particularly for surgery in the head/neck area, as well as after abdominal surgery.

The formation of seromas and/or hematomas after surgery can hinder recovery. While seromas and hematomas will often resolve without intervention, some patients require repeated follow-up visits to have them drained or otherwise treated. Furthermore, the swelling caused by seromas and hematomas will not always fully subside, leading to the formation of an unsightly knot of calcified tissue that can require additional surgical intervention. In addition, the risk of infection can be increased if bodily fluids are not adequately drained from a wound or surgical site.

Surgical drains are currently used to aid in seroma and hematoma management and to provide for fluid drainage at a surgical site. These drains are usually made from synthetic, polymeric materials that must be removed when the drain is no longer needed. The removal of drains has the potential to cause significant irritation and/or discomfort to a patient, and could also result in new wounds or increased scarring, especially when the drains are implanted deeply into a patient's soft tissue.

Accordingly, disclosed herein are decellularized tissue-based drain manifolds comprising at least a portion of an extracellular tissue matrix. The manifolds can be prepared using micro-machining techniques that allow for fluid drainage. The manifolds provide initial rigidity sufficient to resist collapse upon implantation and subsequently soften over time as native cells from tissue surrounding the implant migrate and proliferate within the extracellular tissue matrix of the manifold.

In various embodiments, a tissue-based drain manifold is provided, comprising partially or completely decellularized tissue that has been formed into a sheet, tube, or column and either (a) micro-machined to contain grooves, channels, or holes; and crosslinked; or (b) micronized, reformed into thin strips, rolled to form tubes, and crosslinked. In some embodiments, the tissue-based drain manifolds are crosslinked using e-beam radiation. In certain embodiments, the manifold comprises partially or completely decellularized tissue that has a grid-pattern surface texture. In some embodiments, a manifold comprises multiple rolled tubes linked together with additional strips of decellularized tissue.

In some embodiments, a tissue-based drain manifold further comprises a biocompatible or bioresorbable synthetic component in the form of a hollow tube. The synthetic component may comprise an outer conduit surrounding at least a portion of the partially or completely decellularized tissue in the manifold, or it may comprise an inner conduit surrounded by the partially or completely decellularized tissue in the manifold. In some embodiments, the tissue-based drain manifold further comprises at least one flexible filament (e.g. a bioresorbable synthetic material) attached to the manifold.

In various embodiments, the tissue-based drain manifold is selected to have an initial structural strength approximately equivalent to a synthetic polymer drain that softens over time following implantation in a patient as native cells from tissue surrounding the implant migrate and proliferate within an extracellular matrix in the decellularized tissue. In some embodiments, the initial structural strength is controlled by altering the dose of e-beam radiation or by altering the moisture content of the manifold prior to irradiation.

In some embodiments, a kit is provided; comprising a manifold as described above and instructions for using the kit.

In various embodiments, a method of making a tissue-based drain manifold is provided, comprising: selecting a tissue containing an extracellular matrix; partially or completely decellularizing the tissue; shaping the tissue into the form of a sheet, tube, or column; and either (a) micromachining the tissue to contain grooves, channels, or holes; and crosslinking the tissue; or (b) micronizing the tissue, reforming the tissue into thin strips, rolling the tissue strips to form tubes, and crosslinking the tissue. In some embodiments, the grooves, channels, or holes are prepared using laser micromachining. In some embodiments, the manifold is crosslinked using e-beam radiation. In some embodiments, the decellularized tissue is wrapped around a hollow tube comprising a biocompatible or bioresorbable synthetic material to form an inner synthetic conduit surrounded by the partially or completely decellularized tissue in the manifold. In some embodiments, a biocompatible or bioresorbable synthetic material is wrapped around at least a portion of the decellularized tissue to form an outer synthetic coating surrounding at least a portion of the partially or completely decellularized tissue in the manifold.

In various embodiments, methods of treatment are provided, comprising implanting into a patient in need of fluid management at least one of the tissue-based drain manifolds described herein. In some embodiments, blood or other fluid can drain from the implant site through the tissue-based drain manifold. In various embodiments, the implanted tissue-based drain manifold is not removed from the patient but is repopulated with native cells from tissue surrounding the implant site. In some embodiments, the implanted tissue-based drain manifold has an initial structural strength approximately equivalent to a synthetic polymer drain at implantation and softens over time as native cells from tissue surrounding the implant site migrate and proliferate within an extracellular matrix in the decellularized tissue. In some embodiments, the implanted manifold is fluidly connected to a pump that provides negative pressure to the implant site through the manifold. In some embodiments, the implanted tissue-based drain manifold comprises at least one flexible filament that provides a pathway for channeling fluid at the implant site to the manifold. In certain embodiments, the filament is resorbed over time following implantation.

In various embodiments a tissue-based drain manifold, as disclosed herein, can be implanted following cosmetic surgery, following surgical removal of a tumor, following surgical separation of native tissues, to treat a wound or other void space that occurs through injury or disease, or for any other suitable medical use.

DESCRIPTION OF THE DRAWINGS

FIGS. 1A-C show three examples of tissue-based drain manifolds. The exemplary manifolds have at least one cross-sectional dimension ranging from 2-4 mm and also contain grooves (FIG. 1A), channels (FIG. 1B) or holes (FIG. 1C). FIG. 1A also illustrates the application of a synthetic outer conduit 101 around a tissue-based drain manifold 100 comprising grooves 102, as disclosed below in certain embodiments of the present disclosure.

DESCRIPTION OF CERTAIN EXEMPLARY EMBODIMENTS

Reference will now be made in detail to certain exemplary embodiments according to the present disclosure, certain examples of which are illustrated in the accompanying drawings.

Disclosed herein are tissue-matrix based drain manifolds. In various embodiments, the manifolds are prepared using micro-machining techniques that produce manifolds capable of providing fluid drainage while also providing initial rigidity to resist collapse upon implantation, as well as softening over time as the manifolds are repopulated with native tissue. In some embodiments, thicker tissue harvested from a donor animal is used. In these embodiments, the tissue is decellularized and grooves, channels, and/or holes are carved, e.g., using laser vaporization or other laser micromachining methods, and/or cutting using physical blades that provide for high precision shaping of the holes, grooves, and/or channels (e.g., low variability between the holes, grooves, and/or channels, or low surface roughness produced by cutting or otherwise processing the tissue). In other embodiments, thin strips of particulate (e.g., micronized) or non-particulate decellularized tissue are used. In these embodiments, the tissue is decellularized and rolled to form tubes or other desired shapes. In some embodiments, holes, grooves, and/or channels can also be added to the rolled tissue strips, e.g., using laser vaporization and/or cutting using physical blades. In certain embodiments, the tissue manifolds are cross-linked (e.g., using chemical, dehydrothermal, or irradiation cross-linking). In some embodiments, the cross-linking increases the initial rigidity of the manifold. In certain embodiments, the manifolds have an initial structural strength approximately equivalent to a synthetic polymer drain that softens over time following implantation in a patient as native cells from tissue surrounding the implant migrate and proliferate within the extracellular matrix in the decellularized tissue.

In various embodiments, tissue-based manifolds can be implanted in a similar fashion to conventional surgical drains and/or be used as extensions of conventional drains. In certain embodiments, the manifolds can implanted more deeply than conventional drains within a patient's soft tissue and/or provide an extension of a conventional drain to reach more deeply into a patient's soft tissue because the tissue-based drain manifolds do not need to be removed at the completion of a drainage procedure. In some embodiments, the tissue-based drain manifolds can be connected to a pump or other negative pressure device. Further, in various embodiments, the implanted drains do not require removal but rather are gradually resorbed, providing a natural tissue scaffold for the migration and proliferation of cells from the surrounding native tissue.

The materials and methods provided herein can be used to make a biocompatible manifold or other implantable composition. As used herein, a "biocompatible" composition is one that has the ability to support the migration and proliferation of native cells from surrounding tissue into the composition following implantation and does not elicit a substantial immune response that prevents such cellular activity. As used herein, a "substantial immune response" is one that prevents partial or complete resorption of the implanted material and/or partial or complete repopulation of the implant with native cells.

As used herein, the terms "native cells" and "native tissue" mean the cells and tissue present in the recipient tissue/organ prior to implantation of a tissue-based manifold, or the cells or tissue produced by the host animal after implantation. As used herein, a tissue-based manifold is any piece of tissue intended for use as a manifold in a surgical drainage system, e.g., a piece of partially or completely decellularized tissue intended for use to collect, channel, split, combine, or otherwise direct the flow of a biological fluid in a patient.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

Tissue-Based Drain Manifolds

In various embodiments, a tissue-based drain manifold comprises human or animal tissue that has been at least partially decellularized. The tissue can be acellular, partially decellularized, and/or decellularized tissue that has been repopulated with exogenous cells, so long as the manifold retains at least some of the extracellular matrix components found in the tissue prior to decellularizing.

In certain embodiments, a tissue-based drain manifold can be derived from any human or animal tissue that is suitable for partial or complete decellularization and subsequent implantation. Exemplary tissues include, but are not limited to, bone, skin, dermis, adipose tissue, intestine, urinary bladder, tendon, ligament, muscle, fascia, neurologic tissue, vascular tissue, adipose tissue, vessel, liver, heart, lung, kidney, cartilage, and/or any other suitable tissue. In certain embodiments, a tissue-based drain manifold can include a mammalian soft tissue. For example, in certain embodiments, a tissue-based drain manifold can include partially or completely decellularized mammalian dermis. As another example, a tissue-based drain manifold can comprise partially or completely decellularized mammalian small intestine submucosa, partially or completely decellularized adipose tissue, and/or partially or completely decellularized mammalian lung or liver tissue. A tissue-based drain manifold can comprise tissue from one or more (e.g., 1, 2, 3, 4, 5, or more) different tissue sources. In certain embodiments, the decellularized tissue can come from human or non-human sources. Exemplary non-human tissue sources include, but are not limited to, pigs, sheep, goats, cows, rabbits, monkeys, and/or other non-human mammals. A tissue-based drain manifold can comprise tissue from one or more (e.g., 1, 2, 3, 4, 5, or more) different animal sources.

In some embodiments, a tissue-based drain manifold can be formed from ALLODERM® or STRATTICE™ (LIFE-CELL Corporation, Branchburg, N.J.), which are human and porcine acellular dermal matrices, respectively. Alternatively, any other suitable acellular tissue matrices can be used. For example, a number of biological scaffold materials are described by Badylak et al., and the methods of the present disclosure can be used to produce a stable three-dimensional acellular tissue matrix using any of those materials, or any other similar materials. Badylak et al., "Extracellular Matrix as a Biological Scaffold Material: Structure and Function," *Acta Biornaterialia* (2008), doi:10.1016/j.actbio.2008.09.013, hereby incorporated by reference in its entirety.

In various embodiments, the extracellular scaffold within a partially or completely decellularized tissue may consist of collagen, elastin, and/or other fibers, as well as proteoglycans, polysaccharides and/or growth factors. The tissue matrix may retain some or all of the extracellular matrix components that are found naturally in a tissue prior to decellularization, or various undesirable components may be removed by chemical, enzymatic and/or genetic means. In general, the acellular matrix provides a structural network of fibers, proteoglycans, polysaccharides, and growth factors on which native tissue and vasculature can migrate, grow, and proliferate. The exact structural components of the extracellular matrix will depend on the tissue selected and the processes used to prepare the partially or completely decellularized tissue.

In certain embodiments, a tissue-based drain manifold lacks certain undesirable antigens. For example, certain animal tissues contain alpha-galactose (α-gal) epitopes that are known to elicit reactions in humans. Therefore, tissue-based drain manifolds derived from various animal tissues can be produced or processed to lack certain antigens, such as α-gal. In some embodiments, tissue-based drain manifolds lack substantially all α-gal moieties. Elimination of the α-gal epitopes may diminish the immune response against the manifold. U. Galili et al., *J. Biol. Chem.* 263: 17755 (1988). Since non-primate mammals (e.g., pigs) produce α-gal epitopes, xenotransplantation of acellular tissue matrix material from these mammals into primates may result, in some instances, in rejection because of primate anti-gal binding to the α-gal epitopes on the tissue-based drain manifold. U. Galili et al., *Immunology Today* 14: 480 (1993); M. Sandrin et al., *Proc. Natl. Acad. Sci. USA* 90: 11391 (1993); H. Good et al., *Transplant. Proc.* 24: 559 (1992); B. H. Collins et al., *J. Immunol.* 154: 5500 (1995).

As described in detail below, in various embodiments, tissue-based drain manifolds can be processed to remove antigens such as α-gal, e.g., by chemical or enzymatic treatment. Alternatively, in some embodiments, tissue-based drain manifolds can be produced from animals that have been genetically modified to lack these epitopes.

In certain embodiments, tissue-based drain manifolds comprising human or animal tissue are completely or substantially free of all cells normally present in the tissue from which the manifold is derived. As used herein, "substantially free of all cells" means that a tissue-based drain manifold contains less than 20%, 10%, 5%, 1%, 0.1%, 0.01%, 0.001%, or 0.0001% (or any percentage in between) of the cells that normally grow within the acellular matrix of the tissue prior to decellularization.

In some embodiments, tissue-based drain manifolds can include extracellular scaffolds that have been repopulated with viable cells. Various cell types can be used for repopulation, including stem cells such as embryonic stem cells, adult stem cells (e.g. mesenchymal stem cells), and/or neuronal cells. Any other viable cells can also be used. In some embodiments, the cells are mammalian cells. Such cells can promote native tissue migration, proliferation, and/or vascularization. In various embodiments, the viable cells are applied to the acellular tissue matrix before or after implantation of a tissue-based drain manifold.

In certain embodiments, tissue-based drain manifolds comprise one or more additional agents. In some embodiments, the additional agent(s) can comprise an anti-inflammatory agent, an analgesic, or any other desired therapeutic or beneficial agent. In certain embodiments, the additional agent(s) can comprise, e.g., at least one added growth or signaling factor (e.g. a cell growth factor, an angiogenic factor, a differentiation factor, a cytokine, a hormone, and/or a chemokine). These additional agents can promote native tissue migration, proliferation, and/or vascularization. In some embodiments, the growth or signaling factor is encoded by a nucleic acid sequence contained within an expression vector. Preferably, the expression vector is in one or more of the viable cells that can be added, optionally, to a tissue-based drain manifold. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, initiation and termination codons, etc.) to ensure at least minimal expression of the desired protein by the cell.

Figures 1A, 1B, 1C:
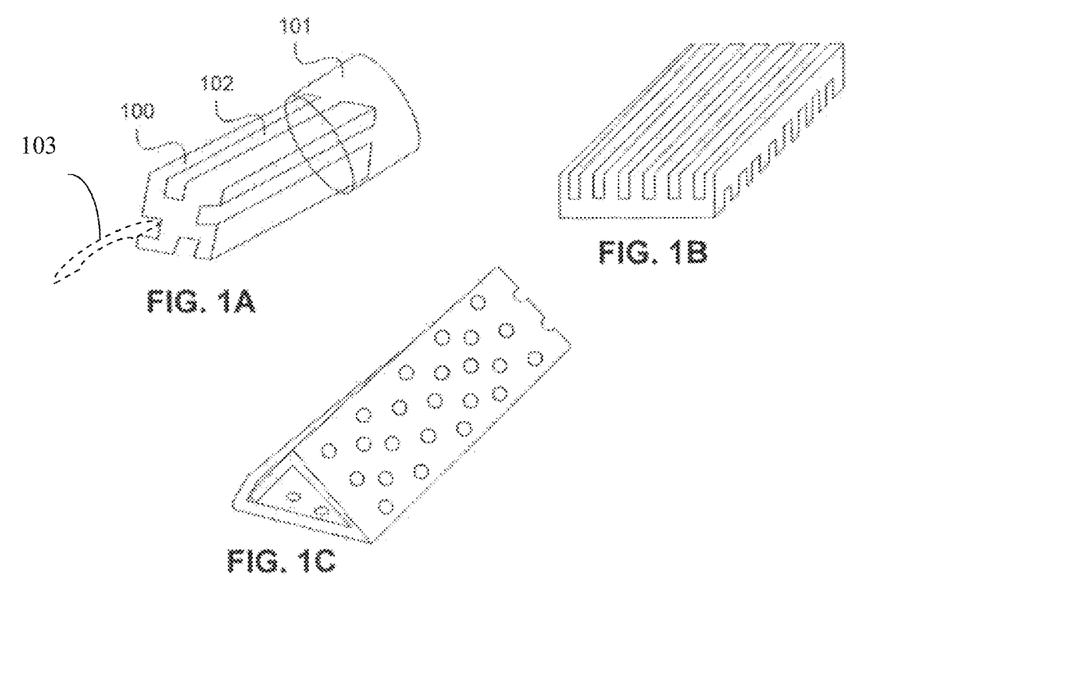

In various embodiments, a tissue-based drain manifold comprises decellularized tissue that has been cut or otherwise shaped to form a tube, column, sheet, or any other desired shape. In some embodiments, the tissue-based drain manifold has at least one cross-sectional dimension of up to about 5 mm (e.g., a dimension of about 5, 4, 3, 2, or 1 mm, or any value in between). In certain embodiments, the tissue-based drain manifold has a length of up to about 20 cm (e.g., about 1, 5, 10, 15, or 20 cm, or any length in between). In some embodiments, the tissue-based drain manifold has grooves, channels, and/or holes carved in it. In some embodiments, the grooves, channels, and/or holes constitute up to about 70% (e.g., about 70, 60, 50, 40, 30, 20, or 10%, or any percentage in between) of the surface area of the manifold and allow for the passage of fluids or pressure through the manifold. Examples of this type of tissue-based drain manifold are shown in FIG. 1A-C. In some embodiments, the grooves or channels are carved to a thickness of about 1.0 to about 3.0 mm in the drain manifolds. In certain embodiments, the holes have a diameter of about 1.0 to about 3.0 mm.

Figure 2:
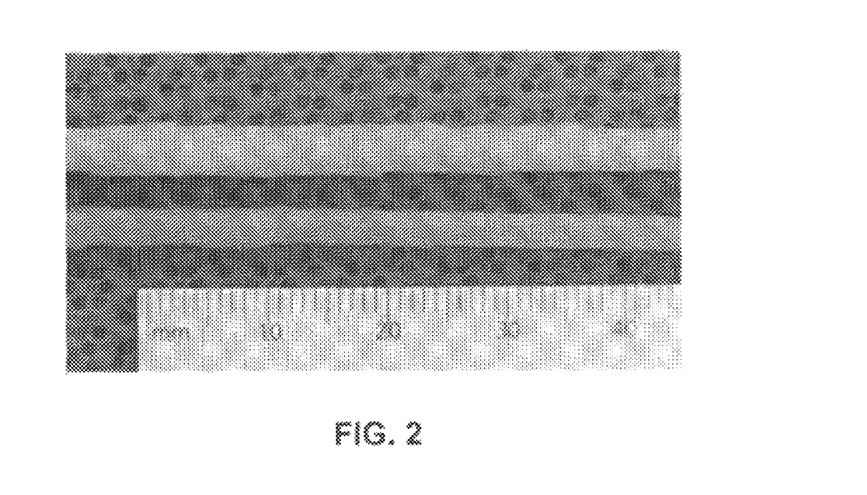
FIG. 2 shows examples of tissue-based drain manifolds comprising rolled strips of decellularized porcine dermis.

In various embodiments, a tissue-based drain manifold can comprise decellularized tissue that has been cut into thin strips and rolled to form a tube or other desired shape. In some embodiments, the thin strips of decellularized tissue comprise decellularized tissue has been shredded, micronized, and/or otherwise homogenized before being reconstituted to form sheets of particulate tissue that are cut to form thin strips. In some embodiments, the thin strips have a thickness of up to about 2 mm (e.g., about 0.5, 1.0, 1.5, or 2.0 mm, or any value in between), a width of up to about 20 mm (e.g., about 1, 5, 10, 15, or 20 mm, or any value in between), and a length of about 20 cm (e.g., about 1, 2, 3, 4, 5, 10, 15, or 20 cm, or any value in between). In some embodiments, a tissue-based drain manifold comprises strips of partially or completely decellularized tissue that have been rolled into a tube or other desired shape. An example of such a tissue-based drain manifold is shown in FIG. 2. In certain embodiments, a tissue-based drain manifold comprising multiple subunits can be linked together using additional thin strips of decellularized tissue to hold the subunits together (e.g., wherein the subunits are brought into contact and the additional thin strips are wrapped around the joints between the subunits to hold the subunits together). In some embodiments, a rolled tissue-based drain manifold has grooves, channels, and/or holes carved in it. In some embodiments, the grooves, channels, and/or holes constitute up to about 70% (e.g., about 70, 60, 50, 40, 30, 20, or 10%, or any percentage in between) of the surface area of tissue-based drain manifold and allow for the passage of fluids or pressure through the manifold. In some embodiments, the grooves or channels are carved to a thickness of about 1.0 to about 3.0 mm in the drain manifolds. In certain embodiments, the holes have a diameter of about 1.0 to about 3.0 mm.

In some embodiments, tissue-based drain manifolds are cross-linked (e.g., using chemical, dehydrothermal, or irradiation cross-linking) in order to retain a desired shape (e.g. a column, sheet, or rolled tube shape) following implantation and/or to provide for increased initial rigidity. In some embodiments, the manifolds are cross-linked using radiation (e.g., e-beam radiation). For example, a manifold can be exposed to between 5 and 50 kGy of e-beam radiation (e.g., about 5, 10, 15, 20, 25, 30, 35, 40, 45, or 50 kGy, or any value in between).

Manifolds lacking cross-linking potentially lack the structural strength needed to function as a drain and/or drain manifold and to provide a conduit for channeling fluid and pressure to an implant site. Accordingly, in various embodiments, cross-linking the manifold can increase the structural strength. For example, a dose of e-beam radiation (e.g., 5-50 kGy) can be selected to impart sufficient cross-linking on the manifold to prevent the manifold from collapsing after implantation and/or to provide a manifold having an initial structural strength approximately equivalent to that of a synthetic drain. In some embodiments, the manifold then softens over time following implantation in a patient as native cells from tissue surrounding the implant migrate and proliferate within the extracellular matrix in the decellularized tissue. In some embodiments, the manifold is eventually repopulated by native cells (e.g., after 2, 3, 4, 5, or more days, or any time period in between), thereby avoiding the need to remove the manifold from the patient at the completion of a drainage procedure.

In certain embodiments, the decellularized tissue in a tissue-based drain manifold has a surface texture, such as a grid pattern, in order to improve fluid flow through the manifold. In some embodiments, tissue-based drain manifolds are sterile. In certain embodiments, the tissue-based drain manifolds are sterilized using radiation, as described infra.

In some embodiments, tissue-based drain manifolds can be used as inserts within or surrounding synthetic drain materials (e.g., polymeric tubing). In certain embodiments, the synthetic component is a hollow tube that can provide increased initial structural strength following implantation and/or can be used as an exterior coating to prevent fluid from diffusing out of the tissue-based manifold into the surrounding implant environment rather than being drained from the patient. An example of a synthetic coating 101 surrounding a tissue-based drain manifold 100 comprising grooves 102 is shown in FIG. 1A. In some embodiments, the synthetic material can be a biocompatible material chosen for its ability to be resorbed by the body after a period of time (e.g., after 1, 2, 3, 4, 5, or more days, or any time period in between). Examples of these materials include, but are not limited to, poly-caprolactone, polylactic acid, polyurethane, polygalacturonic acid, polymer polyglycolic-lactic acid, polyhydroxyalkanoates, polydioxanone or other similar polymers or biological materials known to degrade in vivo.

In various embodiments, a tissue-based drain manifold has increased rigidity initially but softens over time following implantation. In some embodiments, the tissue-based manifold can have an initial rigidity approximately equivalent to the rigidity of a standard polymeric drain such as a polymeric Jackson-Pratt or Brake drain. For example, a tissue-based drain manifold can have an initial rigidity, as measured by compression using a durometer with an OO probe (where readings can vary from 0 (most soft) to 100 (least soft)), of at least about 24 (e.g., at least about 24, 26, 28, 30, 32, 34, 36, 38, or 40, or any value in between), but a reduced rigidity of up to about 22 (e.g., up to about 22, 20, 18, 16, 14, 12, or 10, or any value in between) at least about two days after implantation (e.g., after at least about 2, 3, 4, 5, 6, 7, 8, 9, or 10 days, or any time period in between).

In some embodiments, a tissue-based drain manifold may comprise one or more flexible filaments 103 attached to and extending outward in any direction from the manifold. In some embodiments, these filaments 103 can comprise partially or completely decellularized tissue that has been homogenized, placed in a mold having desired filament shape(s), dried in the mold, and optionally crosslinked to retain the shape of thin filaments. In certain embodiments, the filaments 103 comprise biocompatible and/or resorbable synthetic materials (e.g., poly-caprolactone, polylactic acid, polygalacturonic acid, polymer polyglycolic-lactic acid, polyhydroxyalkanoates, or polydioxanone) in addition to, or in place of, decellularized tissue, and are molded to desired shapes as discussed above for the decellularized tissue filaments. In some embodiments, the filaments 103 have a length of at least about 1.0 mm, and may be as long as about 10 cm (e.g., about 1.0 mm, 5.0 mm, 1 cm, 2 cm, 5 cm, or 10 cm, or any length in between). In certain embodiments, the ultimate length of the filament 103 as used can be determined by the surgeon who can cut the filament 103 to a desired length. In various embodiments, the filaments 103 have at least one cross-sectional dimension of up to about 2.0 mm (e.g., a diameter of about 0.5, 1.0, 1.5, or 2.0 mm, or any value in between). In some embodiments, the filaments 103 provide a pathway down which blood and/or other bodily fluids can flow to reach the tissue-based drain manifold after implantation in a patient.

Tissue-based drain manifolds, as described above, may be packaged as frozen, freeze-dried, hydrated, and/or dehydrated products. In certain embodiments, the packaged tissue-based drain manifolds are sterile. In certain embodiments, the tissue-based drain manifolds are provided in a kit, comprising a packaged tissue-based drain manifold and instructions for preparing and/or using the manifold.

Methods of Making Tissue-Based Drain Manifolds

Disclosed herein are methods of making tissue-based drain manifolds. In some embodiments, the method comprises selecting a tissue containing an extracellular matrix; partially or completely decellularizing the tissue; optionally micronizing the tissue; cutting and optionally rolling the tissue to form a desired shape; processing the tissue to add grooves, holes, and/or other channels; and crosslinking the partially or completely decellularized tissue.

In some embodiments, a tissue-based drain manifold can be prepared from any tissue that is suitable for decellularization and subsequent implantation. Exemplary tissues include, but are not limited to, bone, skin, dermis, adipose tissue, intestine, urinary bladder, tendon, ligament, muscle, fascia, neurologic tissue, vascular tissue, vessel, liver, heart, lung, kidney, cartilage, and/or any other suitable tissue. In certain embodiments, the tissues can include a mammalian soft tissue. For example, in certain embodiments, the tissue can comprise mammalian dermis. In certain embodiments, the dermis can be separated from surrounding epidermis and/or other tissues, such as subcutaneous fat. In certain embodiments, the tissue can comprise mammalian small intestine submucosa or adipose tissue. In certain embodiments, the tissue can include human and/or non-human sources. Exemplary, suitable non-human tissue sources include, but are not limited to, pigs, sheep, goats, cows, rabbits, monkeys, and/or other non-human mammals.

In some embodiments, a tissue-based drain manifold is prepared by partially or completely decellularizing a donor tissue. Exemplary methods for decellularizing tissue are disclosed in U.S. Pat. No. 6,933,326 and U.S. Patent Application 2010/0272782, which are hereby incorporated by reference in their entirety. In some embodiments, the decellularized tissue provides a porous extracellular scaffold structure into which cells from surrounding native tissue can migrate and proliferate after implantation into a host site. In certain exemplary embodiments, the acellular tissue comprises ALLODERM® or STRATTICE™ (LifeCell Corporation, Branchburg, N.J.), which are acellular human dermal products and porcine dermal products, respectively.

In various embodiments, the general steps involved in the production of an acellular or partially decellularized tissue matrix include providing tissue from a donor (e.g., a human cadaver or animal source) and removing cellular material under conditions that preserve some or all of the biological and/or structural functions of the extracellular matrix. In certain embodiments, the tissue can be washed to remove any residual cryoprotectants and/or other contaminants. Solutions used for washing can be any physiologically-compatible solution. Examples of suitable wash solutions include distilled water, phosphate buffered saline (PBS), or any other biocompatible saline solution.

In certain embodiments, the washed tissue can be chemically treated to stabilize the tissue so as to avoid biochemical and/or structural degradation before, during, or after cell removal. In various embodiments, the stabilizing solution arrests and prevents osmotic, hypoxic, autolytic, and/or proteolytic degradation; protects against microbial contamination; and/or reduces mechanical damage that can occur during decellularization of tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

In various embodiments, the tissue can be placed in a decellularization solution to remove viable and non-viable cells (e.g., epithelial cells, endothelial cells, smooth muscle cells, fibroblasts, etc.) from the extracellular matrix without damaging the biological and/or structural integrity of the extracellular matrix. The decellularization solution may contain an appropriate buffer, salt, an antibiotic, one or more detergents (e.g., TRITON X-100™, sodium dodecyl sulfate, sodium deoxycholate, polyoxyethylene (20) sorbitan monooleate, etc.), one or more agents to prevent cross-linking, one or more protease inhibitors, and/or one or more enzymes. In some embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100™ and, optionally, 10 mM, 15 mM, 20 mM, 25 mM, 30 mM, 35 mM, 40 mM, 45 mM, or 50 mM EDTA (ethylenediaminetetraacetic acid) (or any concentration in between). In certain embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of sodium deoxycholate and, optionally, 1 mM, 2 mM, 3 mM, 4 mM, 5 mM, 6 mM, 7 mM, 8 mM, 9 mM 10 mM, 11 mM, 12 mM, 13 mM, 14 mM, 15 mM, or 20 mM HEPES buffer (4-(2-hydroxyethyl)-1-piperazineethanesulfonic acid) containing 10 mM, 15 mM, 20 mM, 25 mM, 30 mM, 35 mM, 40 mM, 45 mM, or 50 mM EDTA (or any concentrations in between). In some embodiments, the tissue is incubated in the decellularization solution at 20, 21, 22, 23, 24, 25, 30, 31, 32, 33, 34, 35, 36, 37, 38, 39, 40, 41, or 42 degrees Celsius (or any temperature in between), and optionally, gentle shaking is applied at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, 48, or 96 hours (or any time in between). The length of time of exposure to the decellularization solution, or the concentration of detergent and/or other decellularizing agents can be adjusted in order to partially or more fully decellularize the tissue. In certain embodiments, additional detergents may be used to remove cells from the tissue sample. For example, in some embodiments, sodium deoxycholate and TRITON K-100™ are used to decellularize and separate other undesired tissue components from the extracellular tissue matrix.

In certain embodiments, the decellularized tissue can be placed in a solution containing calcium hydroxide. In some embodiments, the calcium hydroxide is at a concentration of about 0.05%-1.0% (w/v) calcium hydroxide (e.g., about 0.05, 0.1, 0.15, 0.2, 0.25, 0.3, 0.35, 0.4, 0.45, 0.5, 0.6, 0.7, 0.8, 0.9, or 1.0% w/v) (or any percentage in between). In some embodiments, the tissue is placed in the calcium hydroxide solution at about 20-40° C. (e.g., about 20, 21, 22, 23, 24, 25, 26, 27, 28, 29, 30, 31, 32, 33, 34, 35, 36, 37, 38, 39, or 40° C.) (or any temperature in between). In some embodiments, the tissue is placed in the calcium hydroxide solution for about 1-5 days (e.g., about 1, 2, 3, 4, or 5 days, or any time period in between). In some embodiments, the calcium hydroxide solution serves to dissolve undesired tissue components. For example, where the tissue is dermal tissue, the calcium hydroxide solution can dissolve epidermis and enable the manual removal of hair follicles. In certain embodiments, after calcium hydroxide treatment, the calcium hydroxide can be neutralized, for example using acetic acid.

In some embodiments, after decellularization, the tissue sample is washed thoroughly. Any physiologically compatible solutions can be used for washing. Examples of suitable wash solutions include distilled water, phosphate buffered saline (PBS), or any other biocompatible saline solution. In some embodiments, the wash solution can contain a disinfectant. In certain embodiments, the disinfectant is peracetic acid (PAA), for example at a concentration of 0.05, 0.1, 0.15, 0.2, 0.25, 0.3, 0.4, or 0.5% (or any percentage in between). In certain embodiments, e.g., when xenogenic or allogenic material is used, the decellularized tissue is then treated overnight at room temperature with a deoxyribonuclease (DNase) solution. In some embodiments, the tissue sample is treated with a DNase solution prepared in a DNase buffer (e.g., 20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable DNase buffer can be used, as long as the buffer provides for suitable DNase activity.

While the acellular or partially decellularized tissue in a tissue-based drain manifold may be derived from one or more donor animals of the same species as the intended recipient animal, this is not necessarily the case. Thus, for example, the acellular tissue in a tissue-based drain manifold may be prepared from porcine tissue and implanted in a human patient. Species that can serve as donors and/or recipients of acellular tissue include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice. In some embodiments, tissue from more than one donor animal can be used.

In certain embodiments, decellularized tissue can be treated with one or more enzymes to remove undesirable antigens, e.g., an antigen not normally expressed by the recipient animal and thus likely to lead to an immune response and/or rejection of an implanted tissue-based drain manifold. For example, in certain embodiments, decellularized tissue can be treated with alpha-galactosidase to remove alpha-galactose ($\alpha$-gal) moieties. In some embodiments, to enzymatically remove $\alpha$-gal epitopes, after washing tissue thoroughly with saline, the tissue may be subjected to one or more enzymatic treatments to remove $\alpha$-gal antigens, if present in the sample. In certain embodiments, the tissue may be treated with an $\alpha$-galactosidase enzyme to eliminate $\alpha$-gal epitopes. In one embodiment, the tissue is treated with $\alpha$-galactosidase at a concentration of about 0.2 U/ml prepared in 100 mM phosphate buffered saline at pH 6.0. In other embodiments, the concentration of $\alpha$-galactosidase is reduced to about 0.1 U/ml or increased to about 0.3, 0.4, or 0.5 U/ml (or any value in between). In other embodiments, any suitable enzyme concentration and buffer can be used, as long as sufficient antigen removal is achieved. In addition, certain exemplary methods of processing tissues to reduce or remove alpha-1,3-galactose moieties are described in Xu et al., Tissue Engineering, Vol. 15, 1-13 (2009), which is hereby incorporated by reference in its entirety.

In certain embodiments, animals that have been genetically modified to lack one or more antigenic epitopes may be selected as the tissue source for tissue-based drain manifold. For example, animals (e.g., pigs) that have been genetically engineered to lack expression of the terminal $\alpha$-galactose moiety can be selected as the tissue source. For descriptions of appropriate animals and methods of producing transgenic animals for xenotransplantation, see U.S. patent application Ser. No. 10/896,594 and U.S. Pat. No. 6,166,288, which are hereby incorporated by reference in their entirety.

In some embodiments, the decellularized tissue can be treated to reduce bioburden (i.e., to reduce the number of microorganisms growing on the tissue). In some embodiments, the treated tissue lacks substantially all bioburden (i.e., the tissue is aseptic or sterile). Suitable bioburden reduction methods are known to one of skill in the art, and may include exposing the tissue to radiation. Irradiation may reduce or substantially eliminate bioburden. In some embodiments, an absorbed dose of about 14-18 kGy of e-beam radiation is delivered in order to reduce or substantially eliminate bioburden. In various embodiments, a tissue-based drain manifold is exposed to between about 5 Gy and 50 kGy of radiation (e.g., about 5, 10, 15, 20, 25, 30, 35, 40, 45, or 50 kGy, or any value in between). Suitable forms of radiation can include gamma radiation, e-beam radiation, and X-ray radiation. Other irradiation methods are described in U.S. Application 2010/0272782, the disclosure of which is hereby incorporated by reference in its entirety.

In certain embodiments, after decellularization, viable cells may optionally be seeded in the extracellular matrix of the decellularized tissue. In some embodiments, viable cells may be added to the matrix by standard in vitro cell co-culturing techniques prior to transplantation, or by in vivo repopulation following transplantation. In vivo repopulation can be by the migration of native cells from surrounding tissue into the matrix following implantation of a tissue-based drain manifold, or by infusing or injecting viable cells obtained from the recipient or from another donor into the tissue-based drain manifold in situ. Various cell types can be used, including stem cells such as embryonic stem cells and/or adult stem cells (e.g. mesenchymal stem cells). Any other viable cells can also be used. In some embodiments, the cells are mammalian cells. In certain embodiments, the cells are histocompatible with the subject in which they are implanted. Such cells can promote native tissue migration, proliferation, and/or vascularization. In various embodiments, the cells can be directly applied to the matrix of a decellularized tissue just before or after implantation.

In certain embodiments, one or more additional agents can be added to the extracellular matrix of a decellularized tissue. In some embodiments, the additional agent can comprise an anti-inflammatory agent, an analgesic, or any other desired therapeutic or beneficial agent. In certain embodiments, the additional agent can comprise at least one added growth or signaling factor (e.g., a cell growth factor, an angiogenic factor, a differentiation factor, a cytokine, a hormone, and/or a chemokine). In some embodiments, these additional agents can promote native tissue migration, proliferation, and/or vascularization within the extracellular matrix. In some embodiments, the growth or signaling factor is encoded by a nucleic acid sequence contained within an expression vector. Preferably, the expression vector is in one or more of the viable cells that can be included, optionally, in the extracellular matrix of the decellularized tissue. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

In various embodiments, the decellularized tissue is cut or otherwise processed to form a tube, column, sheet, or other desired shape. In some embodiments, the decellularized tissue is processed to have at least one cross-sectional dimension of up to about 20 mm (e.g., a dimension of about 20, 15, 10, 5, 4, 3, 2, or 1 mm, or any value in between). In certain embodiments, the decellularized tissue is processed to have a length of up to about 20 cm (e.g., about 1, 5, 10, 15, or 20 cm, or any length in between). In some embodiments, grooves, channels, and/or holes are added to the decellularized tissue, for example using blades, needles, or other cutting devices, or using laser vaporization (e.g., an excimer laser at KrF or ArF wavelengths). For example, an Epilog Mini-24™ $CO_2$ Laser system (Epilog Laser, Golden, Colo.) can be used to cut, drill, and/or engrave decellularized tissue using about 65%-100% power and about 25%-75% of the maximum speed setting. In certain embodiments, the grooves, channels, and/or holes constitute up to about 70% (e.g., up to about 70, 60, 50, 40, 30, 20, or 10%, or any percentage in between) of the surface area of the tissue-based drain manifold. In some embodiments, the grooves or channels are carved to a thickness of about 1.0 to about 3.0 mm in the drain manifolds. In certain embodiments, the holes have a diameter of about 1.0 to about 3.0 mm. Exemplary tissue-based drain manifolds comprising grooves, channels, and holes are shown in FIG. 1A-C.

In some embodiments, decellularized tissue is cut into thin strips and rolled to form a tube or other hollow shape. In certain embodiments, the thin strips are cut to have a thickness of up to about 2.5 mm (e.g., up to about 0.5, 1.0, 1.5, 2.0, or 2.5 mm, or any value in between), a width of up to about 20 mm (e.g., up to about 5, 10, 15, or 20 mm, or any value in between), and a length of up to about 20 cm (e.g., up to about 1, 2, 3, 4, 5, 10, 15, or 20 cm, or any value in between). In some embodiments, the strips of tissue are rolled into a tube or other hollow shape. For example, the strips of tissue can be wrapped around a mold, such as a bar or other elongated structure, which is then removed to leave a tissue-based drain manifold comprising a hollow rolled tube. In certain embodiments, a tissue-based drain manifold can be formed by linking together multiple subunits comprising hollow oiled strips of decellularized tissue aligned along their open ends. In some embodiments, the subunits are held together by wrapping additional thin strips of decellularized tissue around the points where the subunits contact each other. In certain embodiments, grooves, channels, and/or holes are added to the rolled tissue, for example using a scalpel, needle, or other cutting device, or using laser vaporization (e.g., an excimer laser at KrF or ArF wavelengths). For example, an Epilog Mini-24™ $CO_2$ Laser system (Epilog Laser, Golden, Colo.) can be used to cut, drill, and/or engrave decellularized tissue using about 65%-100% power and about 25%-75% of the maximum speed setting. In certain embodiments, the grooves, channels, and/or holes constitute up to about 70% (e.g., up to about 70, 60, 50, 40, 30, 20, or 10%, or any percentage in between) of the surface area of the tissue-based drain manifold. In some embodiments, the grooves or channels are carved to a thickness of about 1.0 to about 3.0 mm in the drain manifolds. In certain embodiments, the holes have a diameter of about 1.0 to about 3.0 mm.

In certain embodiments, the thin strips of decellularized tissue that are rolled to form a tissue-based drain manifold comprise micronized tissue. The tissue can be micronized using any suitable technique, for example by blending, shredding, or homogenizing the tissue. In some embodiments, the micronized tissue is then reconstituted to form thin sheets. For example, the micronized tissue can be placed in a sheet of supporting material (e.g., a GAMMA WIPE®, Berkshire Corp., Great Barrington, Mass.) and rolled or pressed (e.g., using a pasta roller) to form thin sheets of micronized tissue. In some embodiments, the thin sheets are crosslinked to increase structural strength using e.g., chemical or hydrothermal methods. In some embodiments, the thin sheets are then cut to form strips that are rolled to make a desired shape, as described above.

In various embodiments, the tissue-based drain manifolds can be cross-linked (e.g., using chemical, dehydrothermal, or irradiation cross-linking) in order to retain a desired shape following implantation. In some embodiments, a cross-linked tissue-based drain manifold can be prepared by contacting the manifold with a chemical cross-linking agent (such as glutaraldehyde, genipin, and/or a reversible cross-linking agent such as 1, 2, 3, 4, 6-pentagalloyl glucose (PGG)). In some embodiments, the cross-linking agent is in a solution at a concentration of about 0.01-2.0% (w/v) (e.g., about 0.01, 0.05, 0.1, 0.15, 0.2, 0.25, 0.3, 0.4, 0.5, 0.6, 0.7, 0.8, 0.9, 1.0, 1.5, or 2.0%, or any percentage in between). In certain embodiments, the cross-linking reaction is allowed to proceed at around room temperature (e.g., about 19, 20, 21, 22, 23, 24, 25, 26, 27, or 28° C., or any temperature in between) for 12-60 hours (e.g., 12, 15, 20, 24, 36, 48, or 60 hours, or any time period in between).

In some embodiments, radiation cross-linking is used, e.g., the tissue-based drain manifold is cross-linked by exposing it to radiation. Suitable forms of radiation can include gamma radiation, e-beam radiation, and X-ray radiation. Other irradiation methods are described in U.S. Application 2010/0272782, the disclosure of which is hereby incorporated by reference in its entirety. In some embodiments, a manifold is cross-linked by exposing it to e-beam radiation. For example, a manifold can be exposed to between 5 and 50 kGy of e-beam radiation (e.g., about 5, 10, 15, 20, 25, 30, 35, 40, 45, or 50 kGy, or any value in between).

In some embodiments, manifolds are exposed to radiation in order to increase their structural strength. For example, a dose of e-beam radiation (e.g., 5-50 kGy) can be selected to impart sufficient cross-linking on the manifold to prevent the manifold from collapsing after implantation and/or to provide a manifold having an initial structural strength approximately equivalent to that of a synthetic drain. In some embodiments, the manifold then softens over time following implantation in a patient as native cells from tissue surrounding the implant migrate and proliferate within the extracellular matrix in the decellularized tissue. In some embodiments, the manifold is eventually repopulated by native cells (e.g., after 2, 3, 4, 5, or more days, or any time period in between), thereby avoiding the need to remove the manifold from the patient at the completion of a drainage procedure.

In various embodiments, the tissue in a tissue-based drain manifold can be decellularized before or after the tissue has been shaped, before or after the tissue has been crosslinked and/or before or after the tissue has been processed to contain grooves, channels, and/or holes.

In some embodiments, textured tissue-based drain manifolds are prepared by using textured tissue that has been partially or completely decellularized. In some embodiments, the tissue can be textured by contacting it with a grid of desired shape and applying pressure to imprint the grid shape on the tissue. In some embodiments, the grid comprises squares having dimensions of about 0.5-3.5 mm (e.g., about 0.5, 1.0, 1.5, 2.0, 2.5, 3.0, or 3.5 mm, or any value in between).

In various embodiments, one or more filaments comprising decellularized tissue or synthetic material can be attached to a tissue-based drain manifold. The one or more filaments can be attached to the drain manifold at any position suitable to enable blood or other bodily fluids to flow down the filament and enter the tissue-based drain manifold. In some embodiments, the filaments are prepared by homogenizing a partially or completely decellularized tissue, reconstituting the homogenized tissue in a mold having a desired filament shape, allowing the homogenized tissue to dry in the mold and, optionally, crosslinking the filaments to help them retain their shape. In certain embodiments, the filaments can comprise biocompatible and/or resorbable synthetic materials (e.g., poly-caprolactone, polylactic acid, polygalacturonic acid, polymer polyglycolic-lactic acid, polyhydroxyalkanoates, or polydioxanone) in addition to, or in place of, decellularized tissue.

Methods of Use

Disclosed herein are methods of using the tissue-based drain manifolds described above.

In various embodiments, one or more tissue-based drain manifolds are implanted to provide channel(s) to bring negative pressure to an implant site and/or to remove blood or other fluids from the implant site. In some embodiments, the manifold is implanted after wound closure or surgical incision to provide for adequate drainage, e.g., after a surgical procedure such as a tumor removal, abdominal surgery, breast implant or other plastic surgery. In certain embodiments, the manifold can be implanted on its own and can provide a conduit for channeling fluid and negative pressure. In other embodiments, the implanted manifold can be surrounded by or placed on top of a synthetic drain material, e.g., in order to increase initial implant strength and/or to prevent the negative pressure and/or fluid from escaping from the implant.

In some embodiments, the synthetic material comprises a hollow tube or sheath that surrounds at least a portion of the tissue-based drain manifold. In other embodiments, the synthetic material comprises a hollow tube or other porous material, and the tissue-based drain manifold is coated or otherwise wrapped around at least a portion of the synthetic material. In certain embodiments, the synthetic material is a biocompatible and/or bioresorbable material that does not need to be removed at the completion of a drainage procedure. Examples of these materials include, but are not limited to, poly-caprolactone, polylactic acid, polyurethane, polygalacturonic acid, polymer polyglycolic-lactic acid, polyhydroxyalkanoates, polydioxanone or other similar polymers or biological materials known to degrade in vivo. An example of a synthetic coating 101 surrounding a tissue-based drain manifold 100 comprising grooves 102 is shown in FIG. 1A.

In various embodiments, one or more tissue-based drain manifolds are retained within the implant site and are resorbed by the migration and proliferation of native cells from tissue surrounding the implant site into the extracellular scaffold provided by the decellularized tissue in the manifolds. In some embodiments, retaining one or more manifolds at the implant site avoids the pain, discomfort, additional tissue damage, and/or additional scarring that could potentially result from removing the implant at the completion of a drainage procedure.

In various embodiments, a tissue-based drain manifold is connected to a conventional fluid drain comprising a polymer or other synthetic material, thereby creating a biocompatible and/or bioresorbable tissue-based drain extension. In some embodiments, the drain extension is implanted at the deepest point within a patient's soft tissue, with the remaining synthetic material extending from the deeply implanted drain extension to the exterior surface of a patient in whom the drain is being implanted.

In various embodiments, the synthetic drain is removed at the completion of a drainage procedure, while the drain extension is retained within the implant site and is resorbed by repopulation of native cells from tissue surrounding the implant site. In certain embodiments, the synthetic drain comprises a biocompatible and/or bioresorbable synthetic material. In some embodiments, the synthetic material, as well as the tissue based drain extension, is retained within the implant site at the completion of a drainage procedure. In certain embodiments, the synthetic material is resorbed following the completion of drainage, while the tissue-based drain extension is repopulated with native cells. In some embodiments, retaining the drain and/or drain extension at the implant site avoids the pain, discomfort, additional tissue damage, and/or additional scarring that could potentially result from removal.

In some embodiments, the implanted tissue-based drain manifold is cross-linked to enhance structural strength, e.g., suing e-beam radiation cross-linking. For example, a manifold can be exposed to between 5 and 50 kGy of e-beam radiation (e.g., about 5, 10, 15, 20, 25, 30, 35, 40, 45, or 50 kGy, or any value in between). In some embodiments, a dose of e-beam radiation (e.g., 5-50 kGy) can be selected to impart sufficient cross-linking on the manifold to prevent the manifold from collapsing after implantation and/or to provide a Manifold having an initial structural strength approximately equivalent to that of a synthetic drain. In some embodiments, the manifold then softens over time following implantation in a patient as native cells from tissue surrounding the implant migrate and proliferate within the extracellular matrix in the decellularized tissue. In some embodiments, the manifold is eventually repopulated by native cells (e.g., after 2, 3, 4, 5, or more days, or any time period in between), thereby avoiding the need to remove the manifold from the patient at the completion of a drainage procedure.

In various embodiments, tissue-based drain manifolds provide initial structural strength after implantation approximately equivalent to that of synthetic drains such as a polymeric Jackson-Pratt or Brake drain. In some embodiments, the initial structural strength of a tissue-based drain manifold, as measured by compression using a durometer with a type OO probe, is at least about 24 (e.g., at least about 24, 26, 28, 30, 32, 34, 36, 38, or 40, or any value in between). In certain embodiments, the tissue-based drain manifold is coated onto, or is surrounded by, a synthetic drain material, thereby increasing the initial structural strength at implantation. In some embodiments, the tissue-based drain manifolds are cross-linked in order to increase their initial rigidity and to help preserve desired manifold shapes following implantation.

In various embodiments, an implanted tissue-based drain manifold (with or without a synthetic component) softens over time as the implant is resorbed and repopulated with native tissue. In certain embodiments, the manifold softens as the components are resorbed and/or repopulated with native cells from surrounding tissue. In some embodiments, a tissue-based drain manifold has a reduced rigidity of up to about 22, as measured by a durometer with a type OO probe (e.g., up to about 22, 20, 18, 16, 14, 12, or 10, or any value in between) at least about two days after implantation (e.g., after at least about 2, 3, 4, 5, 6, 7, 8, 9, or 10 days, or any time period in between). In some embodiments, the implanted manifold does not need to be removed at the completion of a drainage procedure because it is resorbed and/or repopulated with native cells. In certain embodiments, the tissue-based drain manifold comprises cells and/or other factors that promote or enhance repopulation and/or healing at the implant site.

In various embodiments, one or more implanted tissue-based drain manifolds improves healing and/or fluid maintenance at the implant site. In some embodiments, the manifolds provide channels for the delivery of negative pressure to an implant site and for the removal of fluid from the site. In some embodiments, the implanted manifolds comprise decellularized tissue and/or synthetic components that are biocompatible, thereby avoiding inducement of a substantial immune response that could interfere with healing and/or fluid maintenance at the implant site. As used herein, a "substantial immune response" is one that prevents partial or complete healing of native tissue at the implant site, native cell repopulation of the manifolds, and/or fluid drainage by the manifolds. In certain embodiments, implanted tissue-based drain manifolds can lack certain undesirable antigens in order to avoid inducing an immune response. For example, in some embodiments, implanted tissue-based drain manifolds may lack substantially all α-gal moieties that are known to elicit an immune response in humans.

In certain embodiments, the tissue-based drain manifolds that are implanted in a patient comprise human and/or animal tissue that is completely or substantially free of all cells normally present in the tissue from which the manifold is derived. In some embodiments, the implanted tissue-based drain manifolds can include an extracellular scaffold that has been repopulated with viable cells. In various embodiments, the viable cells can be applied to the extracellular scaffold before or after implantation. In certain embodiments, an implanted tissue-based drain manifold can further comprise one or more additional agents. In some embodiments, the additional agent can comprise an anti-inflammatory agent, an analgesic, or any other desired therapeutic or beneficial agent that promotes native tissue healing, native cell repopulation of the manifold, and/or fluid maintenance following implantation. In certain embodiments, the additional agent can comprise, e.g., at least one added growth or signaling factor (e.g., a cell growth factor, an angiogenic factor, a differentiation factor, a cytokine, a hormone, and/or a chemokine). These additional agents can promote native tissue migration, proliferation, and/or vascularization.

Figure 5:
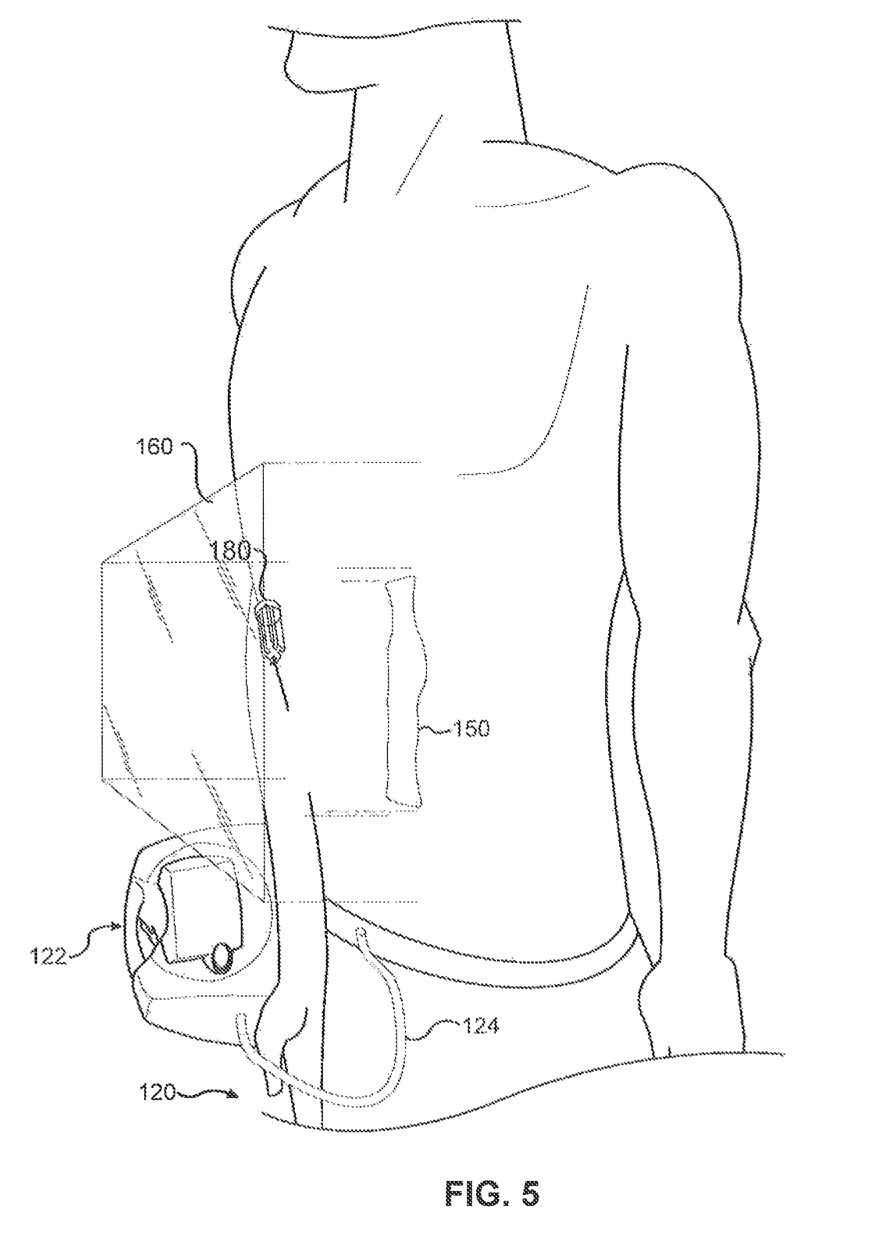
FIG. 5 is an example of a negative pressure wound therapy system, including an exemplary tissue-based drain manifold, as disclosed below in certain embodiments of the present disclosure.

In various embodiments, a tissue-based drain manifold can be used as part of a negative pressure therapy system. For example, FIG. 5 illustrates a negative pressure system, including a tissue-based drain manifold of the present disclosure. As shown in FIG. 5, a negative pressure system can include, in certain exemplary embodiments, a reduced pressure therapy device 120. The reduced pressure therapy device 120 can include a pump 122 fluidly connected to a tissue-based drain manifold 180, e.g., through a fluid passage or tubing 124. The manifold 180 can be placed at the implant site 150. In further embodiments, a drape or dressing 160 is applied over the manifold 180 to seal the epidermis around the implant site 150. In still further embodiments, the fluid passage or tubing 124 passes through the drape 160 to connect the pump 122 and the manifold 180. Accordingly, in certain embodiments the negative pressure therapy device 120 can provide negative pressure from an external negative pressure source 122 to a tissue-based drain manifold 180 at an implant site 150 while maintaining an epidermal seal by passing the tubing 124 through the drape 160.

In certain embodiments of the negative pressure therapy system, a variety of reduced pressure therapy devices can be used. For example, suitable reduced pressure therapy devices include V.A.C.® therapy devices (KCl, San Antonio, Tex.). Such reduced pressure therapy devices can include, in some embodiments, a vacuum pump, similar to the pump 122 shown in FIG. 5. Such devices may also include, in certain embodiments, a flexible sheet 160 to cover the implant site 150 and at least partially seal the implant site. In addition, such systems may include, in various embodiments, one or more tissue-based drain manifolds as described infra. In some embodiments, one or more tissue-based drain manifolds 180 are placed at the implant site 150 and serve to channel negative pressure and/or fluid from the implant site 150. In additional embodiments, the manifolds 180 can facilitate tissue closure and/or healing, and/or be used to help prevent and/or treat infection at the implant site.

In certain embodiments, tissue-based drain manifolds comprising one or more filaments are used as part of a drainage procedure or a negative pressure therapy system. In some instances, the use of a drain or negative pressure system alone (i.e., without a drain manifold comprising one or more filaments) may lead to the build-up of blood or other bodily fluids in distal pockets that cannot be reached by the drain manifold or by the negative pressure system. In such instances, there is a possibility that undesirable seromas and/or hematomas may form. Thus, in certain embodiments, to reduce the risk of seroma and/or hematoma formation and to improve drainage, a tissue-based drain manifold comprising one or more filaments can be implanted into a patient. In some embodiments, the surgeon who implants the tissue-based drain manifold can cut the one or more filaments to desired lengths and position the filaments in appropriate locations at the implant site in order to optimize drainage. In certain embodiments, the filaments provide a pathway to channel blood or fluid to the tissue-based drain manifold, thereby avoiding the undesirable build-up of blood or other bodily fluids at distal locations not reachable by the implanted tissue-based drain manifold and/or by the negative pressure system.

A tissue-based drain manifold can be implanted in a patient as part of any medical procedure in which fluid management is required. For example, tissue-based drain manifolds can be implanted as part of a wound treatment regimen to manage fluid build-up at the wound site. In another example, tissue-based drain manifolds can be used following surgical intervention where drainage and/or other fluid maintenance is required, e.g., to reduce the risk and/or to treat the formation of seromas and/or hematomas following surgery.

EXAMPLES

The following examples serve to illustrate, and in no way limit, the present disclosure.

Example 1: Preparation of Dermal Tissue-Based Drain Manifolds

Drain manifolds can be prepared from dermal tissue harvested from various animals. The thickness and density of dermis vary depending on the species chosen (porcine, bovine and etc.) and the region of the animal from which the dermis is harvested. Dermis that is harvested near the rear spinal area is dense, more rigid, and can have a thickness up to 5 mm. Channels, grooves, and holes can be added to the dermis by laser vaporization, as illustrated in FIG. 1A-C. After decellularization and other tissue processing steps, the micro-machined dermis materials can be used as implantable drain manifolds either on their own, or as an insert within an outer synthetic drain conduit, for management of fluid drainage from a patient.

Alternatively, thin dermal strips harvested from any region of a donor animal can be made into implantable drain manifolds by rolling thin strips of decellularized dermis into a desired shape. In one example, porcine dermis was cut to a thickness of approximately 0.8 mm and decellularized in a solution containing 5.85% sodium chloride, 0.5% Triton X-100 and 0.1 mg/L gentamicin at 37° C. for 24 hours. After 4 washes in saline over a period of approximately 18 hours to remove Triton X-100 residue, decellularized dermal sheets were cut into 10-mm wide tissue strips, which were then disinfected with 0.1% peracetic acid (PAA) for 1 hour. Disinfected tissue strips were rinsed twice in saline. The tissue strips were blot-dried to contain approximately 40-70% water on a mass basis and then rolled on a glass mandrel (ø=1.5~1.8 mm), as illustrated in FIG. 2. The rolled dermal strips were then wrapped with a Gamma Wipe® sheet (55% cellulose and 45% polyester), packaged in foil pouches, and irradiated by e-beam (approximately 16 kGy). After e-beam irradiation, the rolled tissue became stiffer, the shape was stabilized, and stable manifolds of up to 20 cm in length could be prepared.

The thin tissue strips that are rolled to form tissue-based drain manifolds can comprise micronized tissue matrix fibers. For example, decellularized porcine dermis was milled with a Sympak mill at 3400 rpm using a 0.2 Steg rotor and 19T stator (Sympak, Inc., Mundelein, Ill.). Dermal material was run through the Sympak mill four times in Dulbecco's phosphate-buffered saline (PBS) at a ratio of approximately 1 L for every 200 g of decellularized dermal material. The suspension of micronized tissue fibers was centrifuged at 4000 rpm for 10 minutes in order to collect the tissue fibers. A mass of tissue fibers was then placed on a Gamma Wipe® sheet. The sheet was folded around the mass of tissue fibers and placed into a pasta roller at the widest gap setting. Rolling was repeated with progressively narrower gaps before removing the Gamma Wipe wafer and folding half of the wafer back upon itself twice, maintaining the orientation of the fold in the same direction that the wafer was originally extruded. The double-folded material can be re-extruded in the same manner if needed. The Gamma Wipe was then opened on a suitable cutting surface. The micronized and extruded tissue was cut into strips in the same direction as the extrusion. The strips were wrapped around a steel mandrel such that the sides of the strip barely touched each preceding layer of wrapping. The angle of the spiral edges should be about 45 degrees relative to the long axis. The wrapped tissue strips and mandrel were placed into a convection dryer and dried at 45° C. The tissue strips and mandrel were placed in a −80° C. freezer for about 15 minutes, before the mandrel was pulled out of the tissue manifold. Manifolds made in this fashion remain intact upon rehydration.

In addition to rolled tubes, it is possible to form other shapes using the same method. For example, it is possible to make multiple sub-parts, first assembling them with fresh strips of tissue that are used like tape to hold the sub-parts together, before re-applying the heat and dry routine discussed above.

Example 2: Mechanical Testing of Dermal Tissue-Based Drain Manifolds

Figure 3:
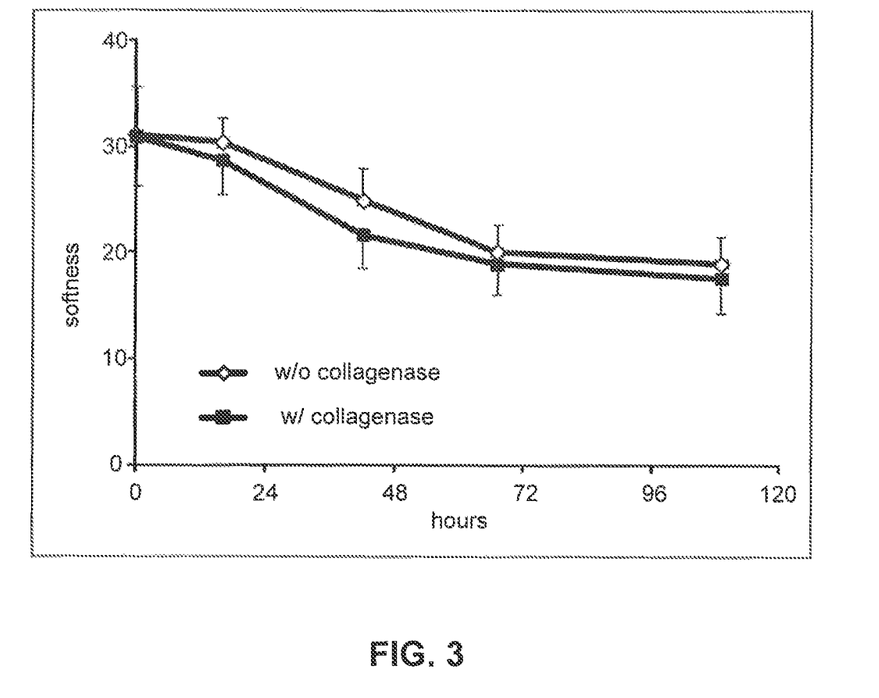
FIG. 3 shows the softness of exemplary tissue manifolds comprising rolled strips of decellularized porcine dermis (3 cm long with a cross-sectional diameter of 2.5-4.0 mm) over time when incubated in 50 mL HEPES buffer at 37° C. with or without collagenase. Incubation time is shown in hours, and softness was measured using a type OO durometer, where readings can vary from 0 (most soft) to 100 (least soft). Diamond data points reflect measurements taken when the manifolds were incubated without collagenase, while square data points reflect measurements taken when the manifolds were incubated with collagenase. Data points reflect the average of 7 tested manifolds, with error bars indicating standard deviation.

Ideally, the tissue-based drain manifolds should be more rigid for the first few days after surgery to facilitate fluid management, and subsequently soften for better integration into patient tissue. To simulate the softening after surgical implantation, tissue manifolds comprising rolled strips of decellularized porcine dermis (3 cm long and 2.5-4.0 mm in diameter) were placed in a conical tube containing 50 mL HEPES buffer (20 mM HEPES, pH=7.4, with 5 mM $CaCl_2$). Sodium azide was added at 0.05% (w/v) to prevent bacterial growth. The manifolds were incubated at 37° C. with or without 0.2 unit/ml collagenase. Softening was tested using a durometer with a type OO probe. Three readings per manifold were taken, and the averaged value was used. The smaller the durometer readings, the softer the manifold. Tissue manifolds had an initial durometer reading of approximately 31, which was reduced to approximately 18 after 5 days of incubation at 37° C. In the presence of collagenase, the manifold softened faster (FIG. 3). For comparison, the softness of Jackson-Pratt silicone drains and Brake silicone drains were tested. The soft Jackson-Pratt silicone drains had an average durometer reading of 18.3+/−2.4 (n=15), and the more rigid Brake silicone drain had an average durometer reading of 52.2+/−5.4 (n=15).

Example 3: Evaluation of Surface-Textured Dermal Tissue-Based Drain Manifolds Porcine dermis was cut to a thickness of 1.2 mm and decellularized in a solution containing 5.85% sodium chloride, 0.5% Triton X-100, and 0.1 mg/L gentamicin at 37° C. for 24 hours. Decellularized tissue was washed in saline four times over a period of approximately 18 hours to remove Triton X-100 residue. Tissue sheets were then treated with 0.1% PAA for approximately 1 hour, then rinsed again twice in saline, and finally stored in saline containing 5% glycerol (w/v). Tissue sheets were blot-dried to contain approximately 40-70% water on a mass basis and then surface-textured by pressing a stainless steel grid (1 mm spacing) onto both sides of the tissue sheet. The textured sheets were then packaged for e-beam irradiation (~16 kGy). Control sheets were not surface-textured.

Figure 4A:
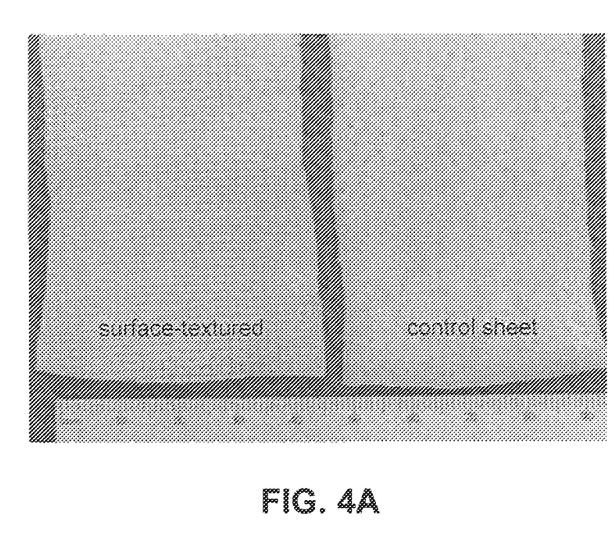
FIG. 4A shows an example of a surface-textured (left) and a non-textured control sheet (right) of decellularized tissue.
Figure 4B:
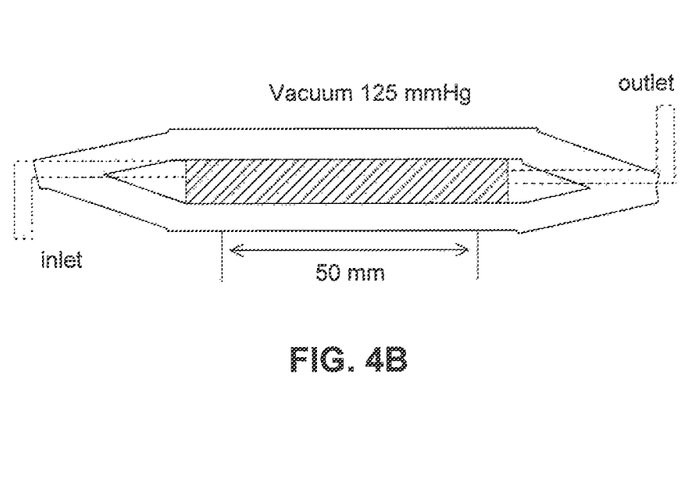
FIG. 4B shows the setup for a fluid flow test to evaluate the effectiveness of fluid removal using surface textured and control tissue sheets. Tissue sheets in a saline solution are placed between silicone layers that are attached to a pump, and the time taken to drain the saline solution from the experimental complex is measured.

Control and surface-textured tissue sheets (FIG. 4A) were fully rehydrated in saline. To examine the performance of textured tissue sheets as drain manifolds, a fluid removal test was conducted using a pressure suction device connected to soft silicone sheets. A tissue sheet was sandwiched between two silicone sheets, and two 1.5 mm drain tubes were connected to either end of the tissue sheet for fluid removal, as illustrated in FIG. 4B. The effectiveness of fluid removal was measured by the time required to remove 40 mL of saline solution dyed with methylene green. The removal time for control sheets was 7.5±3.8 min (N=7) and 3.5±1.5 min (N=7) for surface-textured tissue sheets. Thus, surface-textured tissue sheets permitted faster fluid removal.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A tissue-based drain manifold, comprising partially or completely decellularized dermal tissue that has been formed into a sheet, tube, or column and either
   a. micro-machined to contain grooves, channels, or holes; and crosslinked; or
   b. micronized, reformed into thin strips, rolled to form tubes, and crosslinked; and a biocompatible or bioresorbable synthetic component in the form of an inner conduit surrounded by the partially or completely decellularized dermal tissue in the manifold and an exterior conduit surrounding at least a portion of the partially or completely decellularized dermal tissue in the manifold.

2. The manifold of claim 1, wherein the grooves, channels, or holes are prepared using laser micro-machining.

3. The manifold of claim 1, wherein the partially or completely decellularized dermal tissue in the manifold has a grid-pattern surface texture.

4. The manifold of claim 1, wherein the manifold comprises multiple rolled tubes linked together with strips of decellularized tissue.

5. The manifold of claim 1, wherein the partially or completely decellularized dermal tissue in the manifold is cross-linked using e-beam radiation.

6. The manifold of claim 5, wherein the manifold is exposed to a dose of about 5-50 kGy of e-beam radiation.

7. The manifold of claim 1, wherein an initial structural strength of the manifold is provided by irradiating the manifold and controlling a dose of radiation or a moisture content of the manifold prior to irradiation.

8. The manifold of claim 1, further comprising at least one additional factor selected from an anti-inflammatory agent, an analgesic, a cell growth factor, an angiogenic factor, a differentiation factor, a cytokine, a hormone, and a chemokine.

9. The manifold of claim 8, wherein the at least one additional factor is encoded by a nucleic acid sequence in an expression vector that is contained within one or more viable cells.

10. The manifold of claim 1, wherein the synthetic component comprises at least one of poly-caprolactone, polylactic acid, polyurethane, polygalacturonic acid, polymer polyglycolic-lactic acid, polyhydroxyalkanoates, and polydioxanone.

11. The manifold of claim 1, further comprising at least one flexible filament attached to the manifold.

12. A method of treatment, comprising
    implanting into a patient in need of fluid management at least one tissue-based drain manifold,
    wherein the at least one tissue-based drain manifold comprises a partially or completely decellularized dermal tissue that has been formed into a sheet, tube, or column and either
    a. micro-machined to contain grooves, channels, or holes; and crosslinked; or
    b. micronized, reformed into thin strips, rolled to form tubes, and crosslinked;
    wherein blood and/or other fluid can drain from the implant site through the tissue-based drain manifold;
    wherein the tissue-based drain manifold is not removed from the patient but is repopulated with native cells from tissue surrounding the implant site; and
    wherein the tissue-based drain manifold further comprises a biocompatible or bioresorbable synthetic component in the form of an exterior hollow tube forming an exterior coating surrounding at least a portion of the partially or completely decellularized dermal tissue in the manifold and an inner hollow tube surrounded by the decellularized dermal tissue in the manifold.

13. The method of claim 12, further comprising attaching the tissue-based drain manifold to a synthetic polymeric tubing.

14. The method of claim 13, wherein the synthetic polymeric tubing is fluidly connected to a pump that provides negative pressure to an implant site through the polymeric tubing and the implanted tissue-based drain manifold.

15. The method of claim 14, wherein a drape or dressing covers the implant site and seals the epidermis surrounding the implant, with the synthetic polymeric tubing passing through the dressing from the pump to the implanted tissue-based drain manifold.

16. The method of claim 12, wherein the implanted tissue-based drain manifold further comprises at least one flexible filament that provides a pathway for channeling fluid to the manifold.

* * * * *